United States Patent
Ivorra Cano et al.

(10) Patent No.: US 10,278,521 B2
(45) Date of Patent: May 7, 2019

(54) SYSTEM FOR PREVENTING BACTERIAL INFECTIONS IN NEEDLE TRAJECTORIES

(71) Applicant: UNIVERSITAT POMPEU FABRA, Barcelona (ES)

(72) Inventors: Antonio Ivorra Cano, Barcelona (ES); Quim Castellví Fernández, Barcelona (ES)

(73) Assignee: UNIVERSITAT POMPEU FABRA, Barcelona (ES)

(*) Notice: Subject to any disclaimer, the term of this patent is extended or adjusted under 35 U.S.C. 154(b) by 17 days.

(21) Appl. No.: 14/434,440

(22) PCT Filed: Oct. 22, 2013

(86) PCT No.: PCT/ES2013/000231
§ 371 (c)(1),
(2) Date: Apr. 9, 2015

(87) PCT Pub. No.: WO2014/064304
PCT Pub. Date: May 1, 2014

(65) Prior Publication Data
US 2015/0265751 A1    Sep. 24, 2015

(30) Foreign Application Priority Data

Oct. 25, 2012  (ES) .................................. 201231644

(51) Int. Cl.
*A47F 5/11* (2006.01)
*A61N 1/05* (2006.01)
(Continued)

(52) U.S. Cl.
CPC .......... *A47F 5/112* (2013.01); *A61B 10/0241* (2013.01); *A61B 10/0275* (2013.01);
(Continued)

(58) Field of Classification Search
CPC .......... A61N 1/306; A61N 1/20; A61K 38/00; C07K 14/605; A61M 37/0015
See application file for complete search history.

(56) References Cited

U.S. PATENT DOCUMENTS

| 4,027,393 A | 6/1977 | Ellis et al. |
| 5,154,165 A | 10/1992 | Elliot et al. |

(Continued)

FOREIGN PATENT DOCUMENTS

| EP | 0346058 A1 | 12/1989 |
| ES | 2366845 A1 | 10/2011 |
| WO | WO 2014/064304 | 5/2014 |

OTHER PUBLICATIONS

Ivorra, A. Electrochemical prevention of needle-tract seeding, Annals of Biomedical Engineering, vol. 39, No. 7, Jul. 2011, pp. 2080-2089.

*Primary Examiner* — Sean P Dougherty
*Assistant Examiner* — Patrick Fernandes
(74) *Attorney, Agent, or Firm* — Robert J. Hess; Hess Patent Law Group (57) ABSTRACT

System for preventing bacterial infections in needle trajectories. The system includes
- a percutaneous surgical instrument (1) percutaneously introducible into a patient's tissue (3) such as a biopsy needle, and having an outer surface made of an electrically conductive material;
- a contact electrode (4) applicable to the patient's skin (3*a*);
- a silver coating or element (P) arranged on or forming part of the instrument (1) to break down by electrochemical release when a current is applied thereto, releasing silver ions into its surroundings; and
- an electric current generator (2) arranged and configured for generating a current and inducing the temporary
(Continued)

circulation thereof between the instrument (1) acting as an anode, the tissue (3) and the contact electrode (4) acting as a cathode, respectively, with a specific magnitude and duration for producing a massive and sudden release of silver ions for the purpose of preventing post-treatment bacterial infections.

12 Claims, 2 Drawing Sheets

(51) Int. Cl.
*A61B 10/00* (2006.01)
*A61B 10/02* (2006.01)
*A61B 17/00* (2006.01)
*A61L 31/08* (2006.01)
*A61L 31/16* (2006.01)
*A61M 37/00* (2006.01)
*F16B 12/00* (2006.01)

(52) U.S. Cl.
CPC .............. *A61L 31/088* (2013.01); *A61L 31/16* (2013.01); *A61M 37/00* (2013.01); *A61N 1/0502* (2013.01); *F16B 12/00* (2013.01); *A47F 5/11* (2013.01); *A61B 2010/009* (2013.01); *A61B 2017/00889* (2013.01); *A61L 2300/404* (2013.01); *A61L 2300/606* (2013.01)

(56) References Cited

U.S. PATENT DOCUMENTS

| | | | | |
|---|---|---|---|---|
| 5,578,030 | A * | 11/1996 | Levin | A61B 10/0233 606/39 |
| 5,738,110 | A | 4/1998 | Beal et al. | |
| 6,463,323 | B1 * | 10/2002 | Conrad-Vlasak | A61N 1/205 607/2 |
| 2002/0183582 | A1 * | 12/2002 | Green | A61N 5/1007 600/3 |
| 2005/0154434 | A1 * | 7/2005 | Simon | A61N 1/325 607/116 |
| 2007/0203574 | A1 * | 8/2007 | McGrath | C23C 14/0688 623/1.46 |
| 2008/0199352 | A1 * | 8/2008 | Fuller | A61L 2/03 422/22 |
| 2010/0168829 | A1 | 7/2010 | Schwartz et al. | |
| 2010/0316686 | A1 * | 12/2010 | Dingeldein | A61L 27/306 424/422 |
| 2011/0264030 | A1 * | 10/2011 | Desimone | A61K 9/0009 604/21 |

* cited by examiner

SYSTEM FOR PREVENTING BACTERIAL INFECTIONS IN NEEDLE TRAJECTORIES

FIELD OF THE ART

The present invention generally relates to a system for preventing bacterial infections in biopsy needle trajectories, laparoscopic needle trajectories and the like when these needles, after having been inserted into a target tissue, are withdrawn through tissues existing in the trajectory leading to the target tissue, and in which bacterial infections are prevented by means of applying an electric current to the surgical instrument or needle, and more particularly to a system comprising means for the massive and sudden release of metal ions with antibacterial properties, preferably silver ions.

The system of the present invention is particularly applicable in preventing bacterial infections that occur in needle trajectories defined when performing a biopsy.

PRIOR STATE OF THE ART

A biopsy is a medical diagnostic procedure consisting of taking a tissue sample for subsequent analysis. Said analysis is usually carried out by means of microscopy and sometimes requires treating the sample with biochemical markers and staining for histological analysis.

Biopsies are common in oncology for determining tumor malignancy and type in order to adapt the therapy to be applied to the patient.

A large number of biopsies are performed in a minimally invasive manner by means of sharp instruments in the form of a needle which pierce epithelia of the patient to enter a region in which the tumor to be sampled is located. When piercing said epithelia or other structures forming natural anti-infection barriers, infectious agents such as bacteria are carried along and conduits are established through which said infectious agents can cause infections. In cases in which the pierced barrier is the skin, it is generally easy to prevent said infections by means of hygienic measures and by means of applying antiseptics on the skin. However, on other occasions it is not possible to effectively eliminate the infectious agents and they can cause serious infections. In other words, they can cause iatrogenic infections. One of these cases can be found in prostate biopsies performed through the rectum. In this procedure, the biopsy needle is introduced through the anus and punctures the rectum wall before entering the region of the prostate to be sampled. Infectious agents residing harmlessly in the rectum wall, such as *Escherichia coli* bacteria for example, are therefore carried into regions in which they can cause infections that could become very dangerous. Furthermore, once the biopsy needle is removed, it leaves a hole through which infections can occur due to migration of the infectious agents until the wound closes completely and the anti-infection barrier is restored. Prophylactic measures are normally used in clinical practice to prevent such iatrogenic infections. Some of these measures are hygienic measures, such as the administration of enemas, and others are based on the preventive administration of antibiotics. However, even by adopting these measures, there is a very significant proportion of cases, i.e., between 0.5% and 11%, which result in clinically relevant infections (J Urol. 2003, 169(5):1762-5; Int J Urol. 2008, 15(5):457-9; Br J Urol. June 1996; 77(6):851-5).

There is a wide range of devices for performing biopsies in a minimally invasive manner (examples: CA1253766, U.S. Pat. No. 4,600,014 and US2010198066). However, none of these instruments by itself is capable of preventing problems relating to iatrogenic infections described above.

Some systems which could prevent the spread of tumors in the biopsy needle trajectory and which perhaps could also be used for preventing iatrogenic infections since the problems are similar to a certain extent are known. Therefore, devices are known for acquiring biopsies comprising an invaginated sheath consisting of a flexible material preventing tumor cells from being carried outwards in the insertion trajectory when withdrawing a needle (U.S. Pat. No. 425, 202; Surg. Endosc. 2003, 17(2):311-4). The drawbacks of such devices are the need to modify currently existing biopsy devices, which results in thicker devices, and the fact that these devices do not actually minimize the possible spread of tumor cells or infectious agents caused by cell migration. Furthermore, their current design is envisaged for preventing cells from being carried from the inside out and not from the outside in, which is what would be required to prevent iatrogenic infections.

Methods are also known for producing thermal ablation or cauterization of tissues surrounding the needle trajectory by means of heating the needle, as described in patent documents WO9614018A1 and US2003109802A1, for example, or by means of heating the tissues around the needle trajectory based on the Joule effect with radiofrequency currents, as described by P. F. Laeseke, T. C. Winter 3rd, C. L. Davis, K. R. Stevens, C. D. Johnson, F. J. Fronczak, J. G. Webster and F. T. Lee Jr, in "Postbiopsy bleeding in a porcine model: reduction with radio-frequency ablation-preliminary results" Radiology, vol. 227, pp. 493-499, May 2003, S. A. Dromi, J. Locklin and B. J. Wood, in "Radiofrequency cauterization: an alternative to reduce post-biopsy hemorrhage" Cardiovasc. Intervent. Radiol., vol. 28, pp. 681-682, September-October 2005, and H. Wiksell et al. in "Prevention of tumor cell dissemination in diagnostic needle procedures" British Journal of Cancer, vol. 103, pp. 1706-1709, 2010. Such devices require complete control of the temperature of the needle and its surroundings, which requires at least one temperature sensor in the distal portion of the probe, and therefore modification of the design, since lack of temperature control may result in excessively high temperatures which can make the patient uncomfortable, cause the needle to adhere to cauterized tissue or, on the other hand, constitute insufficient treatment of the tissue surrounding the needle trajectory, in addition to the risk of the heating damaging the samples taken.

Therefore, patent document WO2009156506A1, for example, describes a biopsy needle having two electric conductors connected to a high-frequency generator and arranged such that a high-frequency alternating current produced entirely in the tissue of the patient flows between the ends of said conductors, such that cauterization by heat takes place in the tissue without directly heating the needle, the spread of active tumor cells and bleeding in the needle trajectory thereby being prevented. As regards the need for temperature control, this biopsy needle basically has the same drawbacks as those mentioned above in reference to biopsy needles in which the needle is heated to achieve cauterization. Furthermore, in this needle, like in all thermal systems described above, post-treatment infection would not be effectively prevented since the bacterial proliferation of bacteria migrating through the hole left by the biopsy needle can still occur in treated tissues.

There is a type of solid tumor treatment based on electrochemical reactions which are chemical reactions that take place in the interface between a metal electrode and the biological medium and lead to an electron transfer between the electrode and the biological medium when direct current flows through the interface. These reactions comprise oxidations and reductions involving chemical species of the electrode and biological medium. When released into the biological medium, some of the resulting species can damage tissue components or interfere with biological processes to the extent of compromising cell viability. For solid tumor destruction, these chemical reactions are induced by means of metal needles introduced into the tumor and low currents are applied to said needles, this treatment being referred to as "electrochemical treatment". Current densities in the order of 100 mA/cm$^2$ are normally applied for tens of minutes or even hours to create ablation areas with diameters in the order of several millimeters or a few centimeters. These techniques are also known as "treatment with direct current", "electrolytic ablation" or "electrolysis", although "electrolysis" is used in the field of hair removal in which these reactions are produced close to hair follicles to achieve permanent hair removal.

The article entitled "Electrochemical prevention of needle-tract seeding", *Annals of Biomedical Engineering*, Volume 39, Number 7 (July 2011), pp. 2080-2089, (DOI: 10.1007/s10439-011-0295-4), by Antoni Ivorra, describes a method and system for preventing the spread of tumors in needle trajectories, which is also demonstrated as potentially useful for preventing bacterial infections in needle trajectories; said demonstration is particularly provided in the form of "proof of concept" or experiment conducted with a prototype of the system using an in vitro model based on bacteria.

The system described in said article includes the elements from the preamble of claim 1 of the present invention, although as regards bacterial prevention, it has not been proven in vivo or in tissues, but only in vitro and in a gelatinous preparation suitable for bacterial colonization, the article itself indicating that the numerical conclusions extracted from such in vitro model must not be directly extrapolated to clinical cases since tumor cells and the surroundings thereof are significantly different from the conditions of such in vitro model.

Furthermore, the bacteria studied in the mentioned "proof of concept" are not of the same type as those existing in the mentioned in vivo environments in human tissues.

Operation of the system disclosed in said article is based on generating cathodic electrochemical reactions on the surface of the needle, producing a sufficiently toxic, high pH microenvironment in the tissue surrounding the needle, resulting, in the experiment conducted in an in vitro model, in the electrochemical reactions generated around the needle inactivating bacteria in contact with the needle, and therefore preventing growth of bacterial colonies in the needle trajectory given that the bacteria carried by the needle had previously been inactivated by the increase in pH.

The needle was used as a cathode in all the experiments described in said article, i.e., negative-polarity voltage was applied to the needle, use of the needle as an anode not being suggested in the article.

It is indicated that using the needle as a cathode is more reasonable so that it is not chemically damaged by electrochemical treatment as it is made of an electrochemically soluble material. To that end, such document constitutes a teaching which leads the person skilled in the art away from finding a solution aimed at preventing bacterial infections in needle trajectories that include corrosion of the needle or of a coating thereof.

If the system of said article is used in vivo, the effect of the achieved increase in pH would not remain active (i.e., sufficiently toxic for infectious agents) for more than several minutes or a few hours, because it would be dampened by the organic constituents of living tissues. In other words, the tissues will act as a buffer, and after the end of applying the current, they will end up neutralizing the increase in pH in several minutes or a few hours. Therefore, the risk of infection will return if the wound left by the needle allows infectious agents to migrate from their usually harmless location to those regions in which they can cause harmful infections.

On the other hand, it has been known for centuries that some metals have antimicrobial properties. In particular, silver (Ag) is particularly indicated since it has been observed to have a very strong antibacterial effect and very mild contraindications as well. Said properties do no usually present in solid silver but tend to be more obvious in colloidal silver suspensions or in silver compounds from which silver ions (Ag$^+$) can become detached. Therefore, bandages with silver nitrate are used today to prevent infections in burns and after surgical interventions, for example.

It is also known that the detachment of silver ions from materials containing solid silver can be promoted in electrolytic media (such as living tissues) by means of applying direct currents having positive polarity. Therefore, the use of electrically activated silver electrodes for preventing bone infections (WO2009027968, U.S. Pat. No. 4,027,393) and dental infections (U.S. Pat. No. 4,126,937) has been proposed, for example, said electrodes being implanted in the bone or dental cavities, respectively, so they are not applicable for use in soft tissues.

In said proposals, direct currents are forced to permanently circulate during time intervals in which the antiseptic effect of the prevention or treatment of infections is to be obtained. In other words, a preventive or disinfection treatment is carried out by means of the continuous electrochemical release of silver ions originating from an electrode formed by solid silver, using considerably long application times and small current values in the order of nano- or microamperes, which causes the silver ions to detach very slowly and at a low density. Furthermore, said proposals do not contemplate the antimicrobial effect being able to be prolonged significantly more than the time in which the portion formed by silver is implanted or in contact with the region to be treated.

Nor do the systems described in said proposals relate to systems having a post-treatment effect, treatment only being carried out during the time in which currents are applied to the electrodes.

BRIEF DESCRIPTION OF THE INVENTION

It is necessary to offer an alternative to the state of the art that covers the drawbacks found therein, offering a more efficient and realistic solution for in vivo application in human tissues than that proposed by the pH modification system disclosed in the aforementioned article "Electrochemical prevention of needle-tract seeding", and allows preventing post-treatment bacterial infections for hours or even days.

To that end, the present invention relates to a system for preventing bacterial infections in needle trajectories, comprising in a known manner:

a percutaneous surgical instrument with a proximal end and an electrically conductive distal portion, including a distal end, percutaneously introducible into a tissue of a patient;

a contact electrode applicable to the skin of a patient; and an electric current generator with a first terminal directly or indirectly connected to at least the distal portion of the instrument and a second terminal connected to the contact electrode.

As regards the electrical connection between the first terminal and the electrically conductive distal portion of the instrument, said connection can be carried out in different ways according to the embodiment, such as by means of the surface itself joining the distal portion with the proximal end when said surface is an electrical conductor and the first terminal is connected to the proximal end, or by means of an electrical conductor running through the inside of the instrument and connected at one end to the first terminal and at the other end to the distal portion of the instrument, or in any other manner a person skilled in the art considers suitable for the proposed end.

Unlike known systems, the system proposed by the present invention is characteristically provided for preventing post-treatment bacterial infections, for which it comprises means for the massive and sudden release of metal ions comprising:

a metal coating or element the ions of which have antimicrobial properties with low toxicity for humans, arranged in at least the distal portion of the instrument or forming part of at least said distal portion, which coating or element is configured, sized and provided so as to break down by means of electrochemical release when a current is applied thereto, releasing metal ions into its surroundings, which is said tissue when the instrument is introduced therein; and said electric current generator which is arranged and configured for generating a current and inducing the temporary circulation thereof between the instrument, the tissue and the contact electrode, respectively, with positive polarity in the first terminal and negative polarity in the second terminal, with a specific magnitude and duration for producing said massive and sudden release of metal ions.

According to the embodiment, the system will include the mentioned metal coating or the mentioned metal element, which can in turn be an independent element of the instrument to be arranged therein (through any type of known securing or fixing mechanism considered suitable) or to form all or part of the instrument, as in the case of the instrument containing the metal element as part of an alloy or being formed entirely by the metal element.

Unlike other systems in which metal ions are slowly released from implanted electrodes and do not provide a post-treatment effect, in addition to not including implanted electrodes, the system proposed by the present invention is provided for preventing post-treatment bacterial infections for a long duration, for hours or for days.

On the other hand, another difference of the system proposed by the present invention with respect to said systems of implanted electrodes is that in said systems the silver electrode is introduced for obtaining the effect, i.e., the electrode is expressly designed only for such purpose, whereas in the system proposed by the present invention the electrode from which metal ions are released forms part of another treatment, in this case surgical treatment, the electrode being used during part of the surgical treatment.

This is because as a result of the massive and sudden release of metal ions provided by the system of the present invention, such ions are combined with chloride ions existing in living tissues, forming chloride of the metal in question, preferably silver, in the surrounding areas of the needle, precipitating as a salt due to low solubility and crystals of this compound forming a series of slow and progressive dispensing units causing the metal ions to be released gradually over a prolonged period of time also due to low solubility.

In other words, use of the system proposed by the present invention includes a massive and sudden release of metal ions from the metal coating or element towards living tissues during the induction of current, and a subsequent slow and progressive release of metal ions from the metal chloride compound formed by combining such released ions with chloride ions, which assures the mentioned post-treatment effect with a duration ranging from hours up to days.

Unlike previously mentioned systems in which direct currents are applied during time intervals in which the antibacterial effect is to be obtained, the field of application of the present invention requires very short treatment times so that the system is clinically practical, ideally under a minute or half a minute, which makes it necessary to deal with two phenomena that require limiting current levels and application times. These two phenomena are heating by Joule effect and electrical stimulation.

Living tissues are heated by Joule effect when electric currents are circulated therethrough. The injected heat is determined by the following expression $$q = |J|^2 \rho t = |E|^2 \sigma t$$

where q is the heat generated per unit of volume, $|J|$ is the magnitude of the current density vector, $|E|$ is the magnitude of the electric field vector, $\rho$ is electrical resistivity of the tissue, $\sigma$ is its electrical conductivity ($=1/\rho$) and t is the application time.

To minimize the amount of injected heat, the application time and particularly the magnitude of the applied current density, which will be proportional to the applied current and particularly high around thin electrodes, must be reduced. It is generally considered that a temperature below 55° C. for less than 10 seconds will not cause any tissue damage. Temperature must be reduced for longer exposure times. A temperature of 42° C. can be considered completely safe for times in the order of a few minutes.

According to one embodiment, the instrument is a biopsy needle, the system preferably being provided for performing prostate biopsies, although the system proposed by the present invention is also valid for any case in which the needle pierces or reaches regions in which there are microorganisms that can potentially cause infection when being delocalized and cannot be effectively eliminated by means of topical antiseptics or antibiotics, such as those referring to oral biopsies, endoscopic biopsies, thyroid biopsies, central nervous system biopsies, or any other case in which such risks do exist but are apparently not as common or as damaging as in the case of a prostate biopsy.

The system proposed by the present invention comprises automatic control means configured for starting current supply once the biopsy sample has been taken.

For one embodiment, the magnitude of the current and dimensions of at least the electrically conductive distal portion of the instrument, including the metal coating or element the ions of which have antimicrobial properties with low toxicity, are determined so that the induced current has an average current density measured on the surface of the percutaneously introducible portion of the instrument between 1 mA/cm$^2$ and 1000 mA/cm$^2$, preferably between 1 mA/cm$^2$ and 200 mA/cm$^2$, and even more preferably of substantially 10 mA/cm$^2$.

It is known that passage of direct or low-frequency currents (below 10 kHz) usually causes neuromuscular stimulation with moderate current magnitudes. Said neuromuscular stimulation can cause unwanted effects in the scope of the present invention, such as involuntary movements and pain. In order to prevent said effects, it is appropriate to limit the magnitude of the applied current. In the field of electrochemical ablation or electric hair removal, said effects are prevented by limiting the magnitude of currents to a maximum in the range of 5 to 80 mA.

In the system of the present invention, the magnitude of the current preferably has an instantaneous value (product of current density times the active area of the needle) which will not be less than 1 mA (to minimize treatment time) or greater than 100 mA (to minimize neuromuscular stimulation).

As regards the specific duration of the electric current generator generating the current to be induced, it is between 0.1 and 1000 seconds, preferably between 0.1 and 10 seconds.

For one embodiment, the thickness of the metal coating is comprised between 10 nanometers and 100 micrometers.

At least the metal coating or element the ions of which have antimicrobial properties with low toxicity for humans, and sometimes the entire instrument, can preferably be disposed of after one or multiple uses, the thickness thereof being determined according to the number of uses. In other words, if the same needle is used for obtaining multiple biopsies from one and the same patient (e.g., in the case of a prostate biopsy, 6 or 8 samples are normally taken), for example, the coating must be thick enough so that it does not used up during multiple punctures, being estimated to have a thickness of at least 1 micrometer. In contrast, if the coating is for a single use, it can be less thick.

According to one embodiment, the metal coating or element the ions of which have antimicrobial properties with low toxicity for humans is configured, sized and arranged so that at least 10 µg of silver per $cm^2$ of surface are broken down by means of said massive and sudden release of metal ions during the time corresponding to the mentioned duration determined by use.

According to one embodiment, the biopsy needle is a TRUCUT-type needle, the metal coating or element the ions of which have antimicrobial properties with low toxicity for humans being arranged around the outer surface of the outer needle or forming part thereof.

According to one embodiment, the electric current generator is configured for inverting the polarity of said terminals by applying a current in the opposite direction after the end of the induction of said current with said positive polarity in the first terminal and negative polarity in the second terminal to generate a toxic microenvironment in the tissue around the portion of the instrument introduced therein by means of increasing the pH of the surroundings of the instrument and/or for generating a deposit of oxide particles of the metal in question on the metal coating or element the ions of which have antimicrobial properties with low toxicity for humans.

According to an alternative embodiment, the electric current generator is configured for implementing a sequence with the order inverted with respect to that mentioned in the preceding paragraph, i.e., it is for inducing a current in the opposite direction by applying negative polarity in the first terminal and positive polarity in the second terminal before the start of the induction of current with positive polarity in the first terminal and negative polarity in the second terminal to generate a toxic microenvironment in the tissue around the portion of the instrument introduced therein by means of increasing the pH of the surroundings of the instrument.

For the purpose of carrying out the embodiments that will be described in detail in a following section, the electric current generator is configured for repeating said inductions of current in opposite directions according to a plurality of induction cycles for both of said embodiments.

According to variants of the two alternative embodiments described above, the electric current generator is configured for interposing a pause lasting a determined period of time between the end of the induction of current with positive polarity in the first terminal and negative polarity in the second terminal and the start of the induction of current in the opposite direction, or vice versa.

According to one embodiment, the current induced by the current generator has at least one alternating current component having a frequency between 0.01 Hz and 100 kHz.

For a preferred embodiment, the metal coating or element the ions of which have antimicrobial properties with low toxicity for humans is made of silver or is at least partially formed by silver, the mentioned metal ions being silver ions.

For another not as preferred embodiment, the metal coating or element the ions of which have antimicrobial properties with low toxicity for humans is made of zinc or is at least partially formed by zinc, the metal ions being zinc ions.

The use of materials other than silver or zinc but the ions of which also have antibacterial properties and with low toxicity for humans is also possible.

Likewise, for other embodiments it is also possible to use a combination of the mentioned materials, for example, a combination of silver and zinc.

The system proposed by the present invention enables implementing a method for preventing bacterial infections in needle trajectories, which comprises using the system proposed by the present invention for:

a) performing a massive and sudden release of metal ions into the living tissue in which the instrument is introduced during part of the surgical intervention performed therewith (if the surgical intervention is a biopsy, the ions are generally released once the sample has been taken); and b) performing a slow and progressive release of metal ions into the tissue over a prolonged period of time using slow and progressive metal ion dispensers formed by crystals of the metal in question generated in the surrounding areas of the instrument when the metal ions dispensed in step a) are combined with chloride ions existing in living tissue, thereby assuring prevention of post-treatment bacterial infection.

BRIEF DESCRIPTION OF THE DRAWINGS

The foregoing and other advantages and features will be better understood based on the following detailed description of several embodiments in reference to the attached drawings which must be interpreted in an illustrative and non-limiting manner, in which.

DETAILED DESCRIPTION OF SEVERAL EMBODIMENTS

Figure 1:
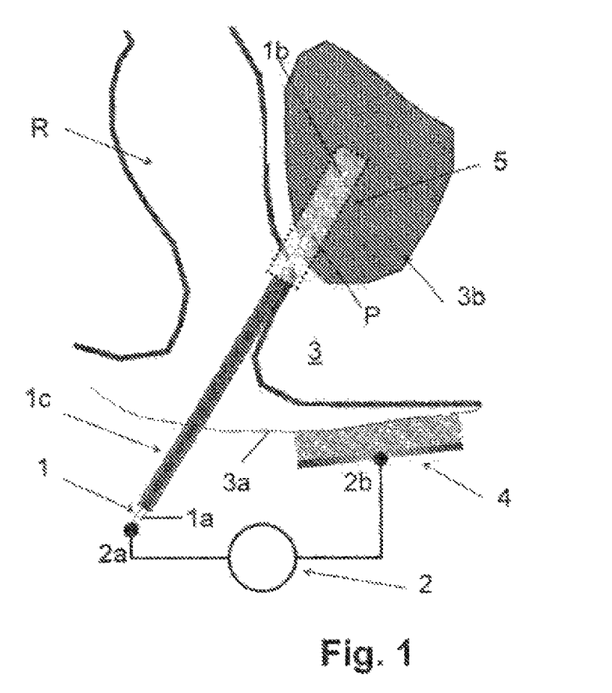
FIG. 1 schematically illustrates the system proposed by the present invention during use for preventing infections in the case of a transrectal prostate biopsy according to an embodiment.

FIG. 1 illustrates all the components of the system proposed by the present invention during use in a transrectal prostate biopsy according to a first embodiment.

Particularly, it can be seen in said FIG. 1 that for the illustrated embodiment the system comprises:

a biopsy needle 1 with a proximal end 1a, an electrically conductive distal portion including a distal end 1b, which is introduced into the prostate 3b of the patient, puncturing the wall of the rectum R which can contain infectious agents, the distal portion and the proximal end 1a being electrically connected to one another;

a contact electrode 4 applicable to the skin 3a of the patient;

a silver coating or element P (or another metal the ions of which have antimicrobial properties with low toxicity for humans), arranged in the distal portion of the biopsy needle 1 or forming part of at least said distal portion, which coating or element is configured, sized and provided so as to break down by means of electrochemical release when a current is applied thereto, releasing silver ions (or another metal ion with antimicrobial properties with low toxicity for humans) into its surroundings, which in FIG. 1 is the tissue 3 including both the prostate 3b and tissues existing in the trajectory from the rectum R to the prostate; and an electric current generator 2 with a first terminal 2a connected to the proximal end 1a of the biopsy needle 1, and therefore to the distal portion, and a second terminal 2b connected to the contact electrode 4, and which current generator 2 is arranged and configured for generating a current (preferably after the sample has been taken inside the biopsy needle 1) and inducing the temporary circulation thereof between the needle 1, the tissue 3 and the contact electrode 4, respectively, with positive polarity in the first terminal 2a and negative polarity in the second terminal 2b (i.e., causing the needle 1 to act as an anode and the contact electrode 4 as a cathode), with a specific magnitude and duration for producing a massive and sudden release of silver ions from the silver coating or element P.

Said silver ions released from the needle 1 are combined with the chemical species of tissues and form new partially stable chemical species causing the toxic environment to remain active for a long time. Particularly, the silver ions are combined with chloride ions existing in the tissue 3, thereby generating crystals of silver chloride which form a slow and progressive dispensing species dispensing silver ions into the tissue 3, thereby assuring prevention of post-treatment bacterial infection by means of the action of said silver ions slowly released by silver chloride, generating a toxic or sterile environment 5, illustrated in FIGS. 1 and 2 as an area demarcated by a dotted line.

Figure 2:
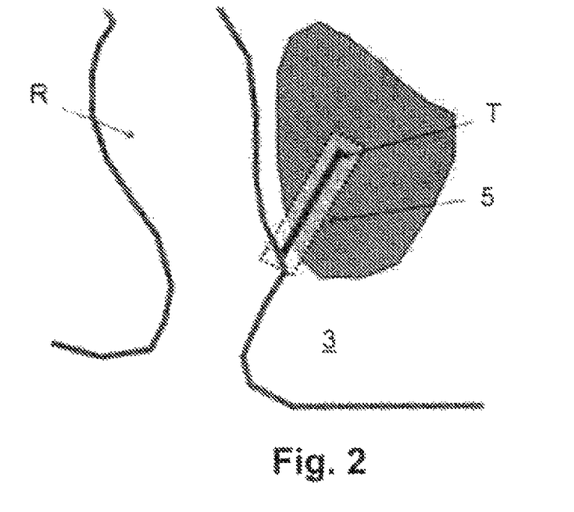
FIG. 2 illustrates for the same embodiment of FIG. 1 the sterile environment around the hole left by the biopsy needle after treatment with current provided by the system proposed by the present invention.

FIG. 2 shows the cylindrical hole T or needle trajectory caused by the biopsy once the needle 1 has been withdrawn from the patient, as well as the ion environment with an antimicrobial effect remaining around the hole T for hours or days.

Different metals (including stainless steel) and the ions they release, since they act as anodes, could be used for the mentioned purpose, but silver (Ag) is particularly suitable because it has been observed to have a very strong antimicrobial effect, and furthermore it has very minor contraindications. Particularly, its microbial capacity against *Escherichia coli* bacteria is very relevant since these bacteria are the main infectious agent related to the problem of infections in transrectal prostate biopsies. In vitro experiments conducted by the authors of the present invention have shown that after applying a direct current of +5 mA for 10 seconds through a silver needle 1 millimeter thick and 5 millimeters long (approximate current density of 30 mA/cm$^2$) in a Petri dish with MacConkey agar (which is suitable for culturing *Escherichia coli* bacteria), growth of *Escherichia coli* bacteria seeded 48 hours after treatment was locally inhibited. In other words, in said experiments the toxic environment, which showed a slightly whitish appearance corresponding to the crystals of silver chloride, remained active for at least 48 hours.

The reactions involving the silver and occurring when a positive current is applied through a silver electrode in living tissue are:

In other words, part of the electrons discharged by the silver electrode forming the needle 1 allow releasing silver ions (Ag+), and these ions are combined with chloride ions existing in living tissues to form silver chloride, as indicated above.

The formation of silver chloride (AgCl) in the surrounding areas of the needle is the fundamental aspect for the persistence of the ion environment with an antimicrobial effect 5 since low solubility of this compound causes silver ions to be released gradually over a prolonged period of time. However, the formation of other chemical species such as silver nitrates and phosphates (in much smaller amounts) and the formation of small silver aggregates in tissue which will also contribute to a prolonged release of silver ions over time cannot be ruled out.

The ranges of currents, average current densities and application times would be those previously indicated in the description of the invention section.

According to a second embodiment, in order to eliminate the widest possible range of pathogenic agents, the first embodiment, i.e., anodic use of the needle 1, can be combined with another already known embodiment relating to cathodic use of the needle 1, by using the needle 1 as a cathode first and then as an anode, or vice versa.

In other words, in this case the current sequence consists of two or three steps: 1—applying current in one direction, 2—a pause without applying current (optional) and 3—applying current in the opposite direction. In other words, the non-specific and instantaneous toxic effect of the increase in pH is combined with the prolonged effect of the metal ion release.

In steps 1 and 3, the ranges of currents, average current densities and application times would be the same as in the cases of the first embodiment.

The pause between steps 1 and 3 will be comprised in the range of from 0 seconds to 100 seconds.

According to the embodiment, steps 1 and 3, and optionally step 2, are cyclically repeated a certain number of times.

It must be pointed out that it has been observed in the field of the electrochemical treatment of tumors that blood circulation in small vessels is interrupted around the cathodes. In the context of the present embodiment, this phenomenon is relevant since the cathodic step will provide the additional advantage of reducing or minimizing post-biopsy bleeding, which is desirable in and of itself because it is one of the possible complications of biopsies, whereby minimizing the migration of infectious agents.

As a result of experimental studies with silver needles, the authors of the present invention have found that it is possible to generate on the needle 1 a deposit of black particles primarily corresponding to silver oxide ($Ag_2O$) and when pulling the needle 1, said silver oxide partially detaches from the needle, being trapped in the tissue 3. This deposit also has antibacterial action, and its extremely low solubility makes it ideal for applications in which the antimicrobial action is to be prolonged for days.

To generate said deposit, current must be cyclically applied such that polarity of the current is inverted. At least one complete cycle in which the current through the needle 1 is first positive (needle 1 as an anode) to then become negative (needle 1 as a cathode) is necessary.

In other words, as in the second embodiment, according to a third embodiment, the first embodiment, i.e., anodic use of the needle 1, can be combined with cathodic use of the needle 1, but in this case, unlike the second embodiment, the needle 1 must first be used as an anode and then as a cathode.

The reactions which would lead to generating silver oxide would be:

$$Ag_{(electrode)} \rightarrow Ag^+ + e^- \quad \text{(needles as an anode)}$$

$$2H_2O + 2e^- \rightarrow H_2 + 2OH^- \quad \text{(needle as a cathode)}$$

$$Ag^+ + OH^- \rightarrow AgOH$$

$$2AgOH \rightarrow Ag_2O + H_2O$$

In other words, the anodic reaction would release silver ions that would then be combined with hydroxide ions generated during the cathodic reaction to form silver hydroxide, which would spontaneously generate silver oxide due to the energy balance of the reaction.

To generate said deposit, one or more cycles of the following sequence applied by the generator and consisting of two or three steps must be performed: 1—applying current in the positive direction (biopsy needle 1 as an anode), 2—optional pause without applying current, and 3—applying current in the negative direction (biopsy needle 1 as a cathode). The cycle can be started in step 3 provided that it returns to said step after having gone through step 1.

Once a cycle has been completed successfully, the remaining cycles do not have to be complete to generate the deposit of black particles.

The pause between steps 1 and 3 will be comprised in the range of from 0 seconds to 100 seconds.

The deposit can also be generated by means of applying a low-frequency alternating current.

In steps 1 and 3, or in half cycles of a low-frequency alternating current, the ranges of currents, average current densities and application times would be the same as in the cases of the first embodiment and second embodiment. In the event of applying alternating current, frequency will be comprised between 0.01 Hz and 100 kHz.

Optional features included in the system of the present invention for other embodiments are:

Advanced Activation Control:

As an alternative to a simple switch or button operated by medical staff to start the application of current before withdrawing the instrument in the form of a needle 1, according to one embodiment, the system according to the present invention is provided with detection means for automatically detecting the start of withdrawal of the needle 1 from the tissue 3. For one variant, these detection means comprise a sensor and an impedance meter connected such that they detect increases in the impedance between the needle 1 and the contact electrode 4, for which purpose the impedance meter can be connected to terminals 2a, 2b of the electric current generator 2, for example, and serving to detect the start of withdrawal of the needle 1 from the tissue 3 through the change in impedance occurring when withdrawal of the needle 1 from the tissue 3 starts. When withdrawal of the needle 1 starts, the relative increase in impedance between the needle 1 and contact electrode 4 can be detected by means of the impedance meter, the corresponding detected signal being able to be used to start up current supply by the electric current generator 2.

On the other hand, the impedance meter can be used as a safety measure as follows: if the impedance meter detects withdrawal of the needle 1 while current is being applied, the system can detect withdrawal and generate a warning signal to alert medical staff to take the necessary measures to prevent possible unwanted effects of, for example, heating, spasms, etc., or also to automatically reduce same as the needle 1 is being withdrawn, and emits a warning only when withdrawal is too rapid. Alternatively, the detection means can comprise an acceleration sensor connected to the proximal end of the needle 1. Progressive activation and deactivation:

For one embodiment, the system according to the present invention comprises current supply control means connected to the electric current generator 2 for progressively increasing electric current supplied by the electric current generator 2 from zero until generating the chosen current density in the portion of the instrument 1 introduced in the tissue 3, and progressively reducing electric current corresponding to the chosen current density from the chosen level to zero before withdrawing the instrument 1. The progressive increase and reduction prevent neuromuscular stimulations that occur when current is applied or cut off abruptly and that result in the patient feeling uncomfortable and even suffering spasms.

Insulating Sheath:

For the embodiment in FIG. 1, the biopsy instrument or needle 1 is provided with an electrically insulating sheath 1c (made of polytetrafluoroethylene or polyethylene, for example) covering part of the metal area of the needle 1. This sheath 1c can be fixed to the needle 1 or be free such that the user (i.e., the doctor) can place it at the location of interest or even cut it before introducing it through the needle to adapt it for use. This sheath 1c has two purposes. On one hand, it will prevent electrochemical reactions from occurring where they are not wanted to prevent unwanted and unnecessary damage (for example, when piercing the skin), i.e., the toxic environment 5 is restricted to the region of interest. On the other hand, the sheath 1c allows improving system efficiency and safety since it reduces necessary current levels for one and the same current density, whereby minimizing the possibility of neuromuscular stimulation, or it allows reducing the application time for a given current.

pH ranges:

When the first terminal of the electric current generator is negative, such that the instrument acts as a cathode, and the second terminal is positive, such that the contact electrode acts as an anode, i.e., for some of the cycles of the second and third embodiments, a current density capable of producing a supraphysiological pH, preferably a pH of at least 8.5, preferably between 10 and 13.8 in said toxic microenvironment, is chosen.

Optional Heating:

According to one embodiment, the system is also designed for applying, together with direct current, an alternating current component (having a frequency greater than 10 kHz) for slightly heating the tissue 3, as in the case of electric hair removal devices.

In those cases in which the increase in temperature does not entail a problem or may even be beneficial because it increases electrochemical treatment efficiency or provides additional advantages such as cauterization, an alternating component can be superimposed on the direct component of the current. A similar strategy is currently used in electric hair removal systems. External electrode with gel and/or a large surface:

According to one embodiment, a conductive gel of the type used in electrophysiology is placed between the skin 3a of the patient and the contact electrode 4 acting as a return electrode. Taking into account that toxic species are produced not only in the needle 1 when electric current is applied but also in the return electrode 4 in the chemical reaction that occurs, the function of this gel is to protect the skin 3a of the patient from damage such as electrochemical burns, i.e., electrical conduction is maintained but the toxic species generated on the surface of the return electrode 4 are prevented from reaching the skin 3a of the patient. The thickness of the gel is about 10 mm, which offers sufficient protection for application times less than 60 seconds and electric fields of 10 V/cm or less of the electric current, because at such magnitudes of the electric field the migration speed of toxic species formed in the anode is about 0.1 mm/s. Alternatively or complementarily, it is also possible to use a large-sized contact electrode (surface more than ten times that of the active area of the biopsy instrument) which prevents electrochemical burns due to the extension thereof on the skin since it produces low concentrations of toxic species incapable of damaging the skin 3a of the patient.
Protection of samples taken in TRUCUT systems:

The electrical sequence will preferably be applied once the sample has been taken. In some biopsy systems (for example, fine needle biopsy systems in which cells are aspirated by means of a syringe), this will mean that the sample will already be far enough away from the region in which treatment will be applied, and therefore there will be no possibility of the sample being affected by treatment. In other biopsy systems, the sample will be confined in a space of the biopsy instrument before the instrument is withdrawn from the patient.

Figure 3:
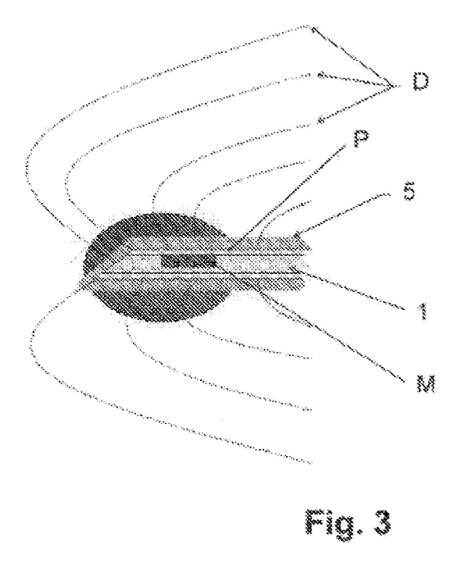
FIG. 3 illustrates a portion of a TRUCUT-type needle after a biopsy sample has been taken therein, at which time

This is the case of TRUCUT-type needles (FIG. 3). Since the sample M that is taken in such needles is located inside the metal needle, when applying currents for treatment said currents will not circulate through the sample M nor will they generate electrochemical reactions on the contact surfaces with the sample M since currents will only circulate through outer surfaces of the needle, as shown in FIG. 3, illustrating current density lines D with a dotted line. In other words, a Faraday cage that will prevent treatment from having an effect on the sample M that is taken will be formed.

Obviously, the foregoing will be valid provided that the inner compartment is sufficiently leak-tight so as to prevent penetration of a significant amount of species electrochemically generated by treatment from the outer surfaces.

A person skilled in the art could introduce changes and modifications in the embodiments which have been described without departing from the scope of the invention as it is defined in the attached claims.

The invention claimed is:

1. A system to prevent needle tract bacterial infections, in biopsy needle tracts, the system comprising:

a metallic, percutaneous surgical instrument with a proximal end and an electrically conductive distal portion, the electrically conductive distal portion including a distal end, the distal end being percutaneously introducible into a tissue of a patient, and the electrically conductive distal portion and the proximal end being electrically connected to one another;

a contact electrode applicable to a skin region of said patient; and an electric current generator with a first terminal directly or indirectly connected to at least the distal portion of said instrument and a second terminal connected to said contact electrode, wherein the instrument is a biopsy needle provided to prevent post-treatment bacterial infections when performing prostate biopsies, for which said instrument comprises a metal coating comprising metal ions having antimicrobial properties with low toxicity for humans, said metal coating being arranged in at least the distal portion of said instrument, and said metal coating being configured, sized and provided so as to break down through electrochemical release when a positive current is applied to the instrument, to produce corrosion of the metal coating and to release said metal ions into said tissue when the instrument is introduced therein;

wherein said electric current generator is arranged and configured to generate said positive current to induce a temporary circulation of the positive current between the instrument, the tissue and the contact electrode, respectively, with positive polarity in the first terminal and negative polarity in the second terminal, said positive current having an average current density measured on a surface of the distal end between 1 $mA/cm^2$ and 1000 $mA/cm^2$, an instantaneous value between 1 mA and 100 mA and a duration of between 0.1 and 60 seconds to produce said break down of the metal coating; and wherein at least 10 μg of metal per $cm^2$ of surface of the metal coating are broken down because of said application of the positive current;

such that, as a result of said release of metal ions, the metal ions will be combined with chloride ions existing in the tissue, forming chloride of the metal coating in a surrounding area of the instrument, wherein said chloride of the metal coating will precipitate as a salt due to low solubility of said chloride of the metal coating, and crystals of the chloride of the metal coating will form a series of dispensing units that will cause the metal ions to be released gradually over a prolonged period of time, assuring an ion environment with antimicrobial effect remaining for hours or days once the instrument has been withdrawn from the patient.

2. The system according to claim 1, wherein a thickness of said metal coating is comprised between 10 nanometers and 100 micrometers.

3. The system according to claim 1, wherein the electric current generator is configured to invert polarity of said terminals by applying an inverted current to generate a toxic microenvironment in the tissue around a portion of the instrument introduced therein by increasing the pH of said surrounding area of the instrument or to generate a deposit of oxide particles of the metal coating, said inverted current being applied after the end of the induction of said positive current with positive polarity in the first terminal and negative polarity in the second terminal.

4. The system according to claim 3, wherein the electric current generator is configured to repeat inductions of said inverted current according to a plurality of induction cycles.

5. The system according to claim 3, wherein the electric current generator is configured to interpose a pause lasting a determined interval of time between said end of the induction of said positive current with positive polarity in the first terminal and negative polarity in the second terminal and a start of induction of said inverted current, or vice versa.

6. The system according to claim 3, wherein said inverted current has at least one alternating current component having a frequency between 0.01 Hz and 100 kHz.

7. The system according to claim 1, wherein the metal coating is made of silver or zinc, said metal ions being silver ions or zinc ions.

8. The system according to claim 1, further comprising:
an electrically insulating sheath covering at least one portion of an electrically conductive outer surface of the instrument, which is selected for correctly regulating the induced positive current, such that the electrically insulating sheath reduces necessary current levels for one and the same current density and thereby minimizes a possibility of neuromuscular stimulation.

9. The system according to claim 4, wherein the electric current generator is configured to interpose a pause lasting a determined interval of time between said end of the induction of said positive current with positive polarity in the first terminal and negative polarity in the second terminal and a start of induction of said inverted current, and vice versa.

10. The system according to claim 1, wherein the electric current generator is configured to invert polarity of the terminals by applying an inverted current to generate a toxic microenvironment in the tissue around a portion of the instrument introduced therein by increasing the pH of said surrounding area of the instrument, said inverted current being applied before the start of the induction of the positive current with positive polarity in the first terminal and negative polarity in the second terminal.

11. The system according to claim 10, wherein the electric current generator is configured to repeat inductions of said inverted current according to a plurality of induction cycles.

12. The system according to claim 10, wherein said inverted current has at least one alternating current component having a frequency between 0.01 Hz and 100 kHz.

* * * * *